United States Patent [19]

Yokoi et al.

[11] Patent Number: 4,757,819
[45] Date of Patent: Jul. 19, 1988

[54] ULTRASONIC ENDOSCOPE

[75] Inventors: Takeshi Yokoi, Hachioji; Masahiro Kawashima, Hino; Koichi Matsui, Tokyo; Yasuhiro Ueda, Kokubunji; Michio Sato; Akibumi Ishikawa, both of Hachioji, all of Japan

[73] Assignee: Olympus Optical Co., Ltd., Tokyo, Japan

[21] Appl. No.: 50,710

[22] Filed: May 14, 1987

[30] Foreign Application Priority Data

May 21, 1986 [JP] Japan ................................ 61-116667
Oct. 31, 1986 [JP] Japan ................................ 61-259758

[51] Int. Cl.⁴ ........................ A61B 1/00; A61B 10/00
[52] U.S. Cl. ........................................ 128/660; 128/4
[58] Field of Search ..................................... 128/660, 4

[56] References Cited

U.S. PATENT DOCUMENTS 4,375,818  3/1983  Suwaki et al. ........................... 128/4
4,391,282  7/1983  Ando et al. ........................... 128/660
4,489,728  12/1984  Matsuo et al. ........................ 128/660
4,494,549  1/1985  Namba et al. ........................ 128/660

Primary Examiner—William E. Kamm
Assistant Examiner—George Manuel
Attorney, Agent, or Firm—Frishauf, Holtz, Goodman & Woodward

[57] ABSTRACT

An ultrasonic endoscope according to the present invention comprises an insertion portion having a hard distal end portion. A first holding member is provided to the hard distal end portion, and an ultrasonic vibrator is mounted on the first holding member. A second holding member, detachably mounted with respect to the first holding member, is provided at the hard distal end portion, and an observation optical system is mounted on the second holding member. The second holding member is fixed to the first holding member by a fixing means. In the ultrasonic endoscope with the above arrangement, the first holder for holding the ultrasonic vibrator can be separated from the second holder for holding the observation optical system.

10 Claims, 16 Drawing Sheets

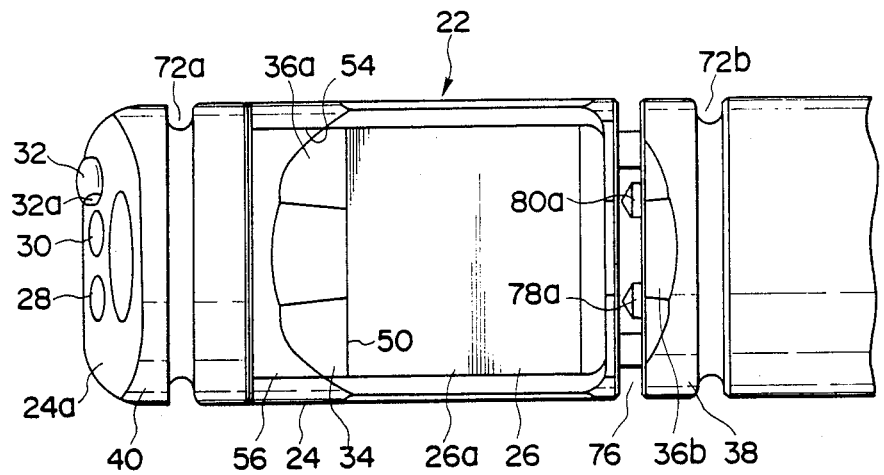
F I G. 4
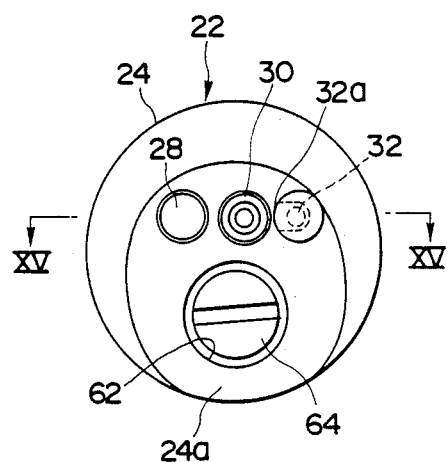
F I G. 5

ULTRASONIC ENDOSCOPE

BACKGROUND OF THE INVENTION

A. Field of the Invention

The present invention relates to an endoscope including an insertion portion having a hard distal end portion and, more particularly, to an ultrasonic endoscope incorporating an ultrasonic vibrator at its hard distal end portion.

B. Description of the Prior Art

In a known ultrasonic endoscope, an ultrasonic vibrator for transmitting/receiving an ultrasonic wave is mounted on, e.g., a hard distal end portion of an insertion portion of the endoscope, and the ultrasonic wave is scanned by the ultrasonic vibrator, thereby observing, e.g., a tomographic image of a body cavity wall. In such an ultrasonic endoscope, a concave ultrasonic vibrator mounting portion for incorporating the ultrasonic vibrator, and insertion holes for receiving a bundle of optical fibers of an observation optical system, e.g., a light guide and an image guide, are formed in a main body of the hard distal end portion. The ultrasonic vibrator is fixed in the ultrasonic vibrator mounting portion of the hard distal end portion by an adhesive and the like, and the bundle of optical fibers of the observation optical system is fixed in the insertion holes of the hard distal end portion by an adhesive and the like.

As a conventional example, in an ultrasonic endoscope disclosed in Japanese Patent Disclosure (Kokai) No. 57-200136, a bundle of optical fibers of an observation optical system, e.g., a light guide and an image guide, is embedded in a support block, an ultrasonic vibrator is placed in a space of a housing portion of the support block, and a filler material is filled in a space around the ultrasonic vibrator, thereby fixing the ultrasonic vibrator integrally with the support block.

In addition, in an ultrasonic endoscope disclosed in Japanese Utility Model Disclosure (Kokai) No. 57-26207, a recess for incorporating an ultrasonic vibrator is formed in a main body of a distal end constituting portion, and insertion holes for receiving a bundle of optical fibers such as an image guide of an observation optical system and a light guide of an illumination optical system are formed in the distal end constituting portion. The ultrasonic vibrator is fixed in the recess by an adhesive and the like, and the bundle of optical fibers is inserted in the insertion holes and fixed therein by an adhesive and the like. That is, the ultrasonic vibrator, the bundle of optical fibers, and the like are fixed in the main body of the distal end constituting portion, respectively.

Furthermore, in an endoscope disclosed in Japanese Patent Disclosure (Kokai) No. 55-96132, an ultrasonic vibrator is detachably mounted on the distal end of a distal end constituting portion by an electrical connecting means such as a connector.

A large number of signal cables are connected to a typical ultrasonic vibrator. In addition, a plurality of pipes such as an air-supply channel and a treatment tool insertion channel together with optical fibers of an observation optical system are housed in an insertion portion of an endoscope. For this reason, when a signal cable of the ultrasonic vibrator is disposed in the insertion portion of the endoscope, an inner space of the insertion portion becomes extremely small. Therefore, when the insertion portion is to be bent during an operation of the endoscope, the bundle of optical fibers, the pipes, and the signal cables of the ultrasonic vibrator disposed in the insertion portion interfere with each other, thereby posing a problem in which the bundle of optical fibers is cut.

However, in a conventional ultrasonic endoscope, the ultrasonic vibrator and the bundle of optical fibers of the observation optical system are fixed integrally with each other in the main body of the hard distal end portion. Therefore, when the bundle of optical fibers of the observation optical system is damaged, the expensive ultrasonic vibrator which normally operates must be replaced together with the damaged bundle of optical fibers, resulting in high cost.

SUMMARY OF THE INVENTION

It is, therefore, an object of the present invention to provide an ultrasonic endoscope in which when a bundle of optical fibers of an observation optical system is damaged, only the damaged bundle of optical fibers can be replaced.

The above object is achieved by the following ultrasonic endoscope. That is, the endoscope includes an insertion portion having a hard distal end portion, a first holding member is provided to the hard distal end portion, and an ultrasonic vibrator is mounted on the first holding member. A second holding member, detachably mounted with respect to the first holding member, is provided at the hard distal end portion, and an observation optical system is mounted on the second holding member. The second holding member is fixed to the first holding member by a fixing means.

Therefore, in the ultrasonic endoscope with the above arrangement, the first holder for holding the ultrasonic vibrator can be separated from the second holder for holding the observation optical system. As a result, when a bundle of optical fibers of the observation optical system, e.g., a light guide or an image guide is damaged, only the damaged bundle of optical fibers can be replaced, thereby reducing repairing cost.

BRIEF DESCRIPTION OF THE DRAWINGS

FIG. 4 is a bottom view of a distal end portion shown in FIG. 3;

FIG. 5 is a front view of the distal end portion shown in FIG. 3;

DETAILED DESCRIPTION OF THE PREFERRED EMBODIMENTS

Figure 1:
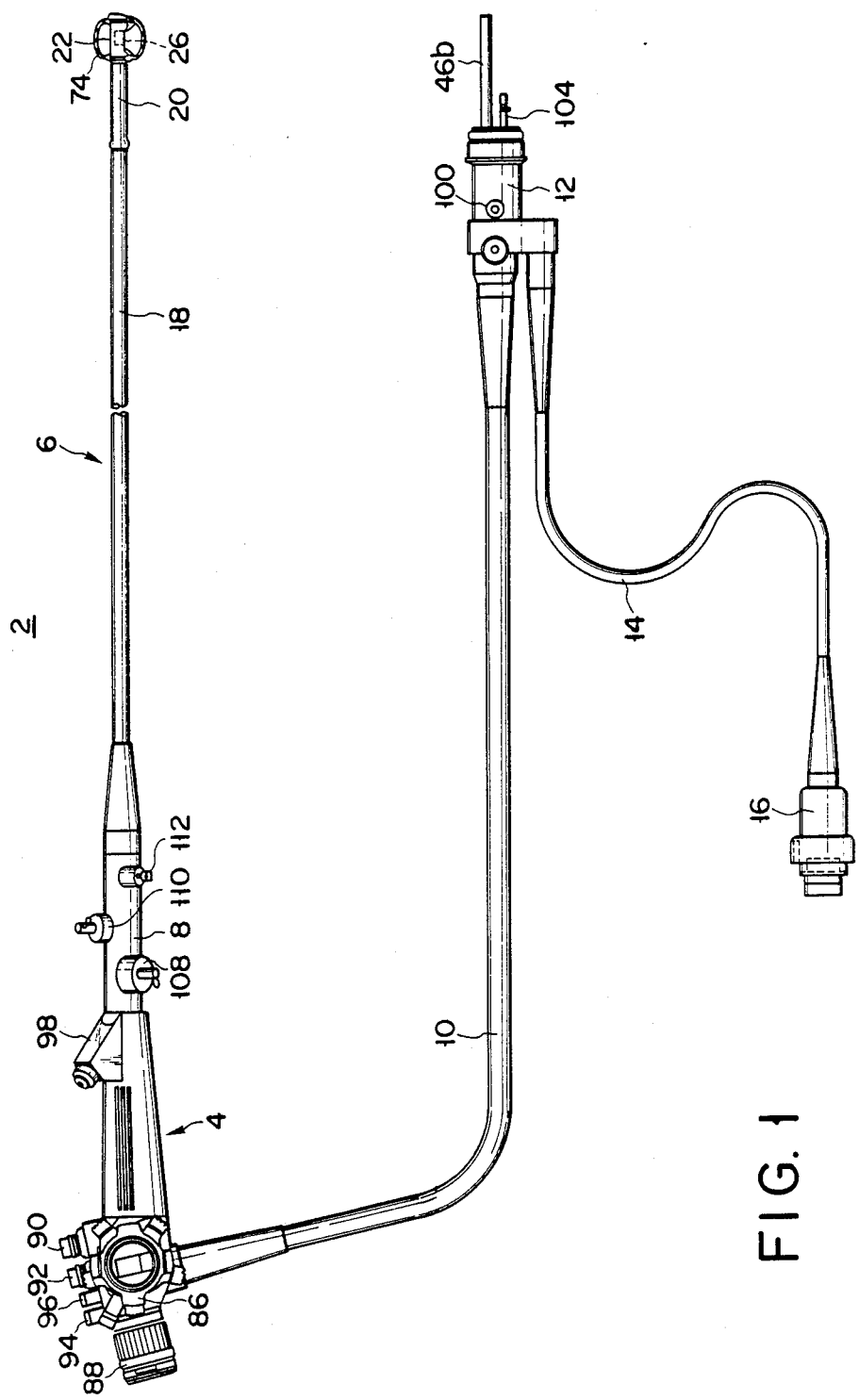
FIG. 1 is a side view showing an overall outer appearance of an ultrasonic endoscope according to the present invention.
Figure 2:
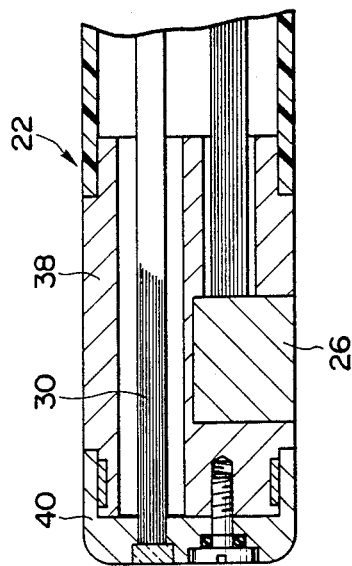
FIG. 2 is a schematic longitudinal sectional view of a hard distal end portion of the ultrasonic endoscope shown in FIG. 1.

Embodiments of the present invention will now be described below with reference to the accompanying drawings. FIGS. 1 to 21 show a first embodiment of an ultrasonic endoscope according to the present invention. As shown in FIG. 1, ultrasonic endoscope 2 includes manipulating portion 4, insertion portion 6, and sub-manipulating portion 8 provided therebetween. Universal cord 10 is connected to portion 4. Connector 12 of the endoscope is mounted on the distal end portion of cord 10. Electrical connector 16 is connected to connector 12 through electrical cable cord 14. Connector 12 of cord 10 is connected to a light source unit (not shown), and connector 16 of cord 14 is connected to an ultrasonic observation unit (not shown). In addition, hard distal end portion 22 is coupled to the distal end of flexible portion 18 of portion 6 through bending portion 20.

Figure 3:
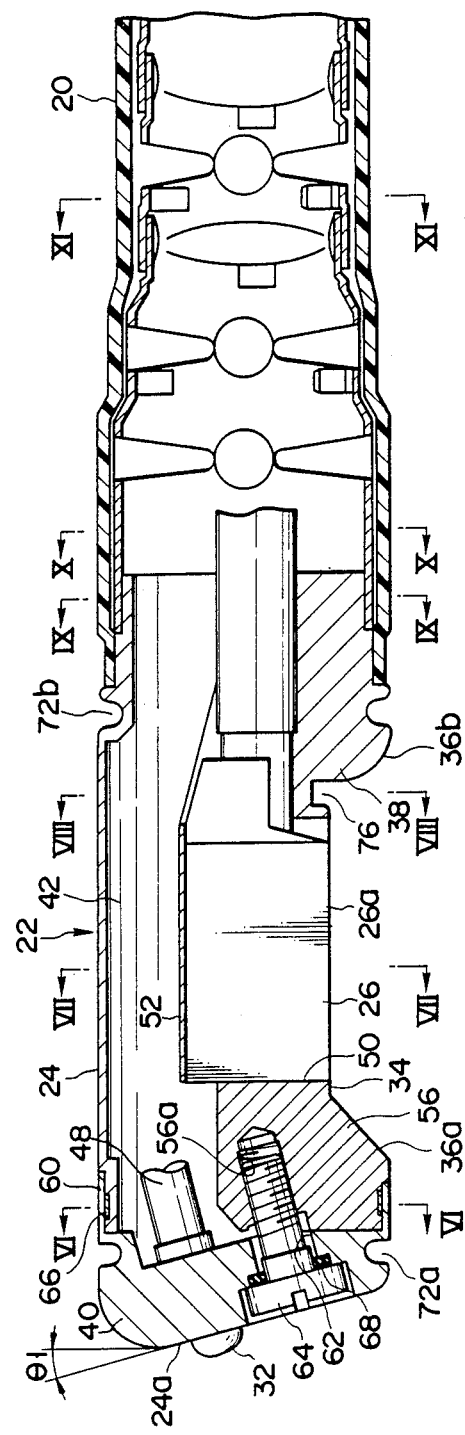
FIG. 3 is a longitudinal sectional view of a hard distal end portion of an ultrasonic endoscope according to the first embodiment of the present invention.

As shown in FIGS. 3 and 4, array type ultrasonic vibrator 26 is incorporated in main body 24 of hard distal end portion 22. In this first embodiment, distal end face 24a of body 24 is so formed as to be inclined at a proper angle $\theta 1$ (about 15°) with respect to a direction orthogonal to an axial direction. As shown in FIG. 5, suction-forceps port 28 is formed in face 24a of body 24, and the distal end face of observation optical system 30 and air-supply/water-supply nozzle 32 are respectively mounted thereon. In addition, recess 34 is formed in a side surface of body 24, and ultrasonic transmitting-/receiving surface 26a formed on a surface of vibrator 26 is mounted on a bottom portion of recess 34 and is exposed outwardly. Furthermore, chamfered portions 36a and 36b inclined along a direction from the bottom portion of recess 34 to an outside portion thereof are formed on a front side surface and a rear side surface, respectively. Therefore, when electronic sector type vibrator 26 for a longitudinal slice is mounted on body 24, portions 36a and 36b eliminate a problem in which a diagnostic range is narrowed by both the side surfaces of recess 34.

Figure 6:
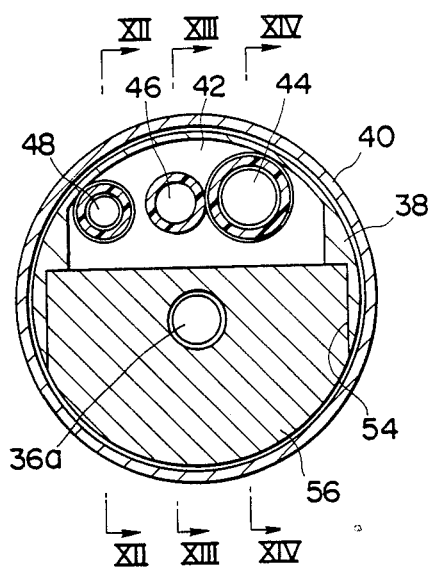
FIG. 6 is a cross-sectional view of the hard distal end portion of the endoscope taken along the line VI—VI in FIG. 3.
Figures 7, 8:
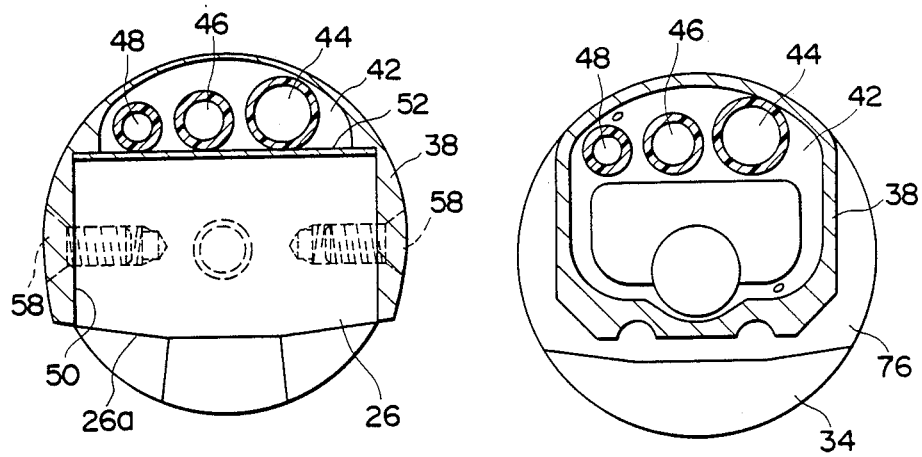
FIG. 7 is a cross-sectional view of the hard distal end portion of the endoscope taken along the line VII—VII in FIG. 3.
FIG. 8 is a cross-sectional view of the hard distal end portion of the endoscope taken along the line VIII-—VIII in FIG. 3.

Body 24 includes first holder 38 for holding vibrator 26 and second holder 40 for holding system 30. In the first embodiment, holder 40 is formed by the distal end portion of portion 24, and holder 38 is disposed behind holder 40. As shown in FIGS. 6 to 9 and FIGS. 12 to 14, insertion hole 42 having a relatively wide opening area is formed inside holder 38 to extend from the front end face to the rear end face thereof. Treatment tool insertion channel 44, optical fiber bundle 46 such as a light guide and an image guide of system 30, and air-supply/-water-supply pipe 48 are respectively provided in hole 42. In addition, hole 42 is connected to holding portion 50 for holding vibrator 26. In the first embodiment, partition plate 52 is disposed between vibrator 26 held by portion 50 and hole 42, as shown in FIGS. 3 and 7. An adhesive with a good thermal conductivity such as an epoxy adhesive mixed with a powder of SiC (silicon carbide) is coated on a bonding surface between vibrator 26 and portion 50 of holder 38. In addition, as shown in FIGS. 4 and 6, notch 54 is formed in holder 38 at the front side portion of portion 50 while portion 50 is connected to holder 38, and embedded member 56 is embedded in notch 54. Member 56 is embedded in notch 54 of holder 38 and fixed by set screws 58 (shown in FIG. 7 by broken line) to holder 38.

As shown in FIG. 3, bending portion 20 is connected to a proximal end of distal hard portion 22. The bending portion 20 has a number of tubular segments 21 rotatably connected to one another by connection pins 23. Flexible sheath 25 surrounds the outer peripheral surfaces of tubular segments 21. The distal-end tubular segment 21 is attached to a proximal end portion of first holding member 38. The proximal-end tubular segment 21 (not shown) is connected to a distal end portion of flexible portion 18. Bending portion 20 can be bent in a desired direction by manipulating portion 4 through a wire (not shown).

On the other hand, as shown in FIG. 3, cylindrical outer fitting portion 60 fitted on the distal end portion outer surface of holder 38 and screw insertion hole 62 are formed in holder 40 for holding system 30. Second holder set screw 64 to be inserted in screw insertion hole 62 is threadably engaged with screw hole 56a of member 56. Portion 60 of holder 40 is fitted on the distal end portion outer surface of holder 38 so that holder 40 is detachably coupled to holder 38 by second holder set screw 64. In addition, sealing member 66 is interposed between the inner surface of portion 60 of holder 40 and the distal end portion outer surface of holder 38, and O-ring 68 is mounted between screw 64 and holder 40. For this reason, good waterproof and air-tight properties between holders 40 and 38 are assured by sealing member 66 and O-ring 68.

Figure 12:
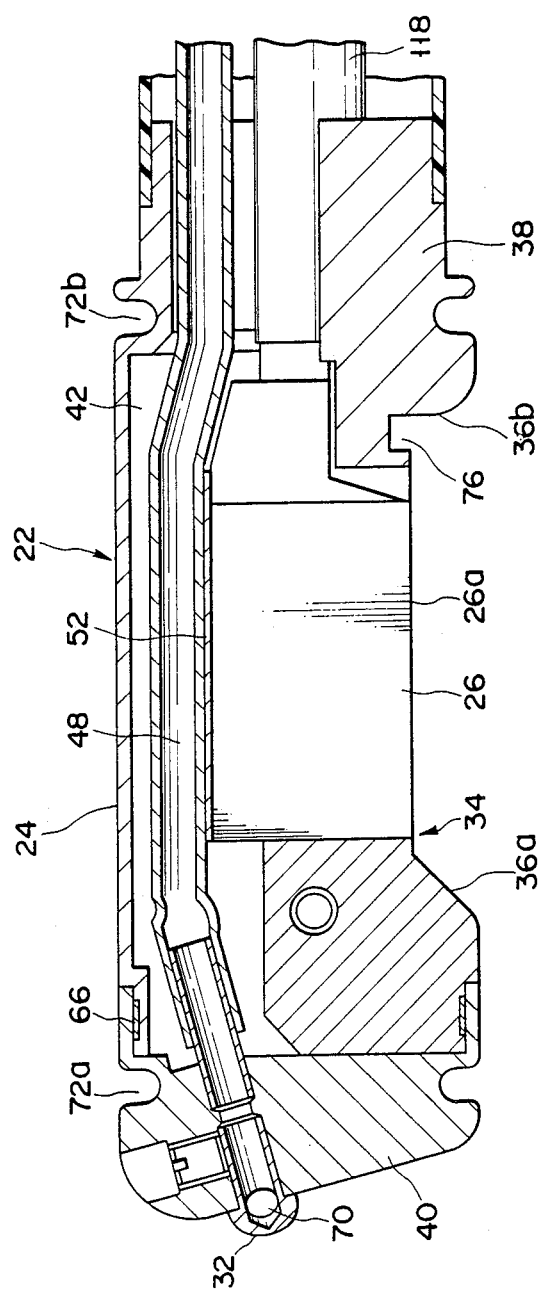
FIG. 12 is a cross-sectional view of the hard distal end portion of the endoscope taken along the line XII—XII in FIG. 6 and FIG. 33.
Figure 13:
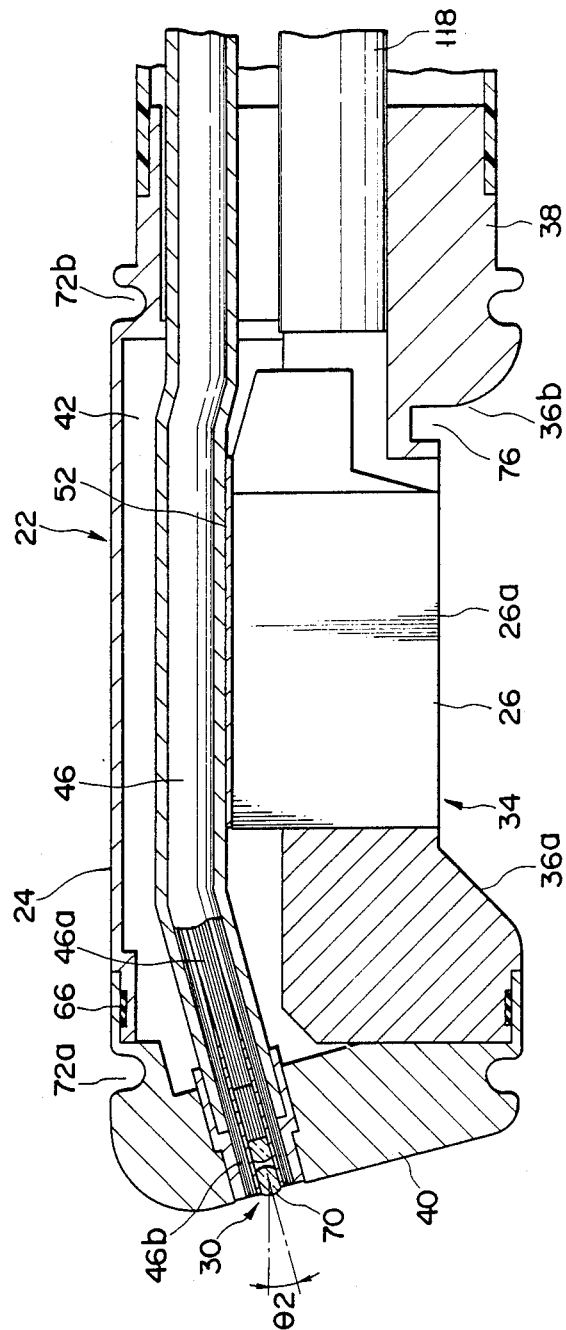
FIG. 13 is a cross-sectional view of the hard distal end portion of the endoscope taken along the line XIII—XIII in FIG. 6 and FIG. 33.
Figure 14:
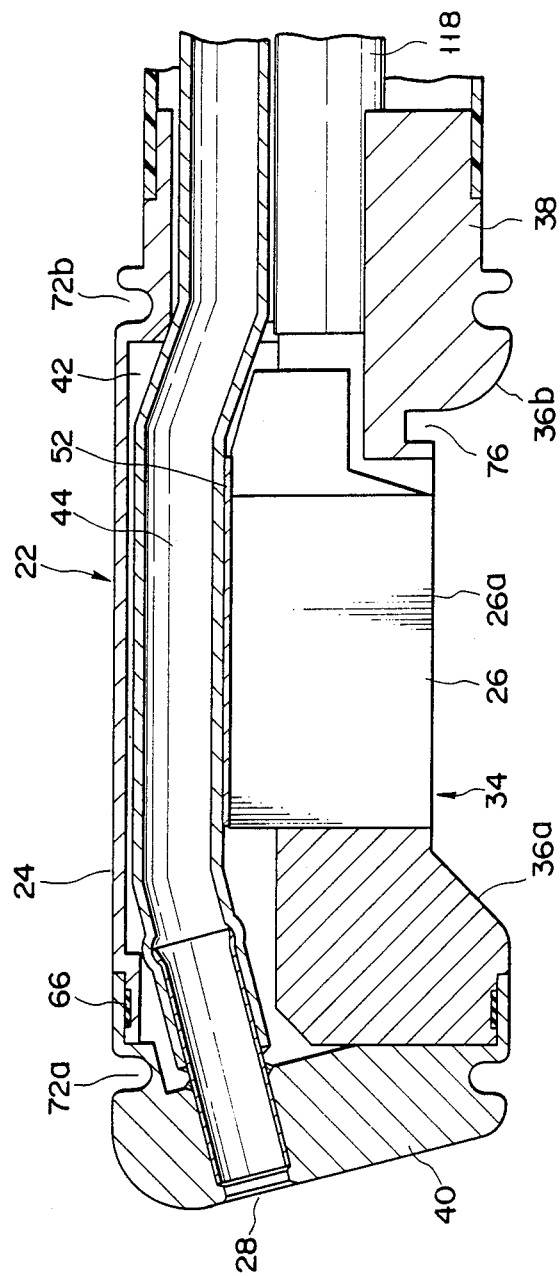
FIG. 14 is a cross-sectional view of the hard distal end portion of the endoscope taken along the line XIV—XIV in FIG. 6 and FIG. 33.
Figure 15:
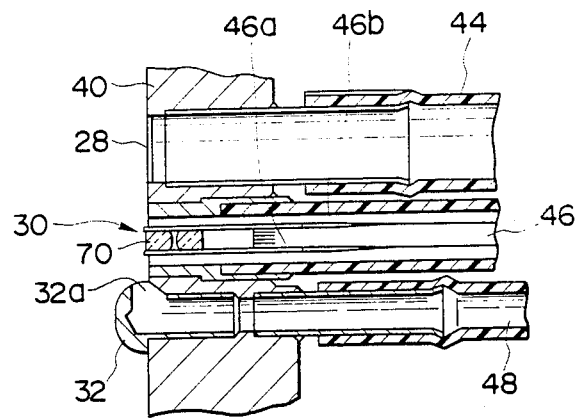
FIG. 15 is a cross-sectional view of the hard distal end portion of the endoscope taken along the line XV—XV in FIG. 5 and FIG. 33.

Nozzle 32 disposed on the distal end face of holder 40 is coupled to air-supply/water-supply pipe 48, as shown in FIGS. 3 and 12. The distal end face of system 30 is disposed between port 28 and nozzle 32, as shown in FIG. 5. In addition, injection port 32a of nozzle 32 faces the distal end face of system 30, as shown in FIGS. 5 and 15. Therefore, water or air supplied through pipe 48 can be injected from port 32a of nozzle 32 toward the distal end face of system 30. As shown in FIG. 13, bundle 46 such as the light guide and the image guide of system 30 includes image guide portion 46a and ring-like light guide portion 46b provided on an outer surface of portion 46a, i.e., portions 46a and 46b are formed in single bundle 46. In this embodiment, objective lens 70 is disposed on the distal end face of system 30 so as to oppose the distal end of portion 46a of bundle 46, and the distal end portion of portion 46b of bundle 46 extends to a position of the outer surface of lens 70. A light beam guided through portion 46b of bundle 46 is emitted from the distal end face of portion 46b so as to be inclined at proper angle $\theta 2$ (about 15°) toward a mounting surface of vibrator 26 with respect to an axis of body 24.

Figure 16:
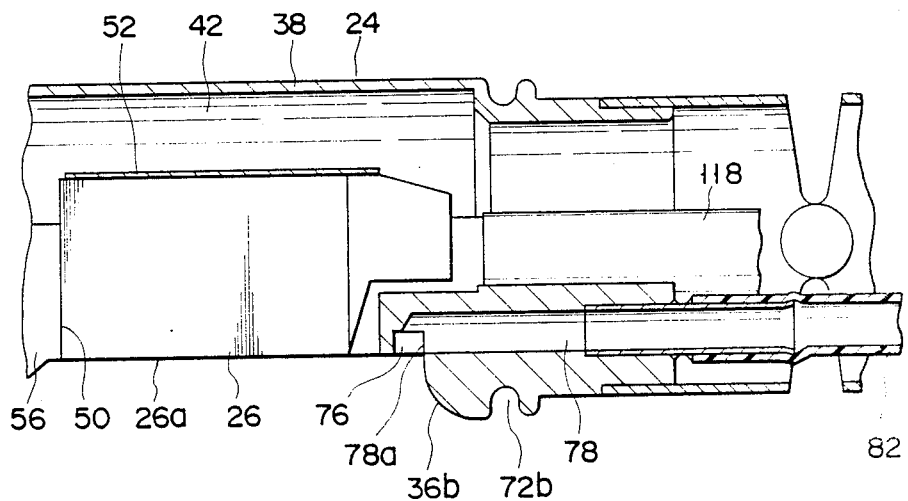
FIG. 16 is a longitudinal sectional view of a balloon water-supply path according to the first embodiment.
Figure 22:
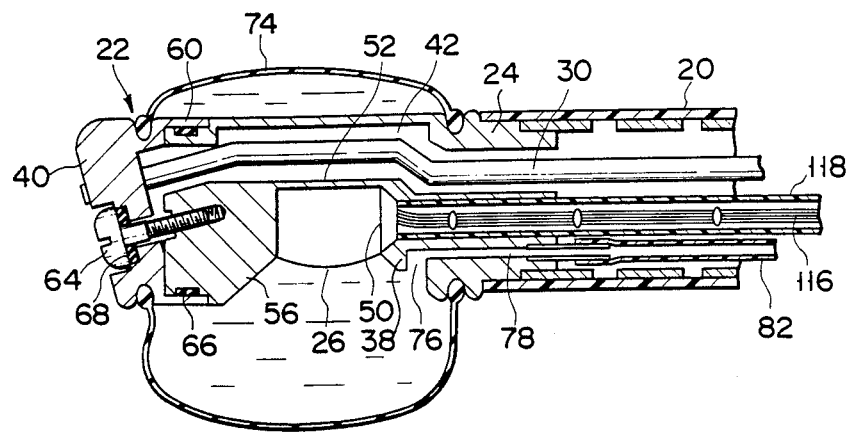
FIGS. 22 and 23 are side views showing a first modification of the hard distal end portion according to the first embodiment of the present invention.

Ring-like balloon mounting grooves 72a and 72b are provided at both end portions of the outer surface of body 24. One groove 72a is formed on the outer surface of holder 40, and other groove 72b is formed on the outer surface of holder 38, respectively. As shown in FIG. 22, O-ring portions are respectively formed at both the end portions of balloon 74 made of an elastic member such as rubber having elasticity. O-ring portions of balloon 74 are formed and mounted in grooves 72a and 72b, respectively, and the entire outer surface of body 24 is covered with balloon 74. In addition, concave communication groove 76 is formed on the outer surface of holder 38 so as to extend along a circumference between the mounting portion of vibrator 26 and groove 72b as shown in FIG. 16. Furthermore, balloon water-injection hole 78 coupled at its one end to groove 76 and balloon suction hole (not shown) having the same arrangement as that of hole 78 are respectively formed at the proximal end of holder 38. Ends of balloon water-injection pipe 82 and balloon suction pipe (not shown) are respectively coupled to the other ends of hole 78 and the balloon suction hole. Water is supplied into groove 76 from pipe 82 and hole 78 through balloon recess water-injection hole 78a between hole 78 and groove 76, and is also supplied into balloon 74 through groove 76. When water is supplied into balloon 74, air in balloon 74 is simultaneously sucked from a balloon suction port (not shown) between groove 76 and the balloon suction hole sequentially through the balloon suction port and the balloon suction pipe.

Portion 4 shown in FIG. 1 includes bending knob 86 for bending flexible portion 20 of portion 6, eyepiece 88, air-supply/water-supply piston 90, and suction piston 92. Release switch 94 for remote-controlling an instrument such as a camera and release switch 96 for freezing an image of a monitor camera and the like of the ultrasonic observation unit are respectively disposed near pistons 90 and 92, and treatment tool insertion port member 98 is formed near a coupling portion of portion 8. In addition, each piston main body of pistons 90 and 92 is incorporated in a cylinder to be movable along an axial direction. A water inlet port, an air inlet port, a water outlet port, and an air outlet port are formed in a cylinder of piston 90, and an air exhaust hole is formed in the piston main body of piston 90. When the piston main body of piston 90 is held at a normal position where it is projected, the water inlet and outlet ports are kept closed, the air inlet and outlet ports are kept open, and the air exhaust hole of the piston main body keeps communicating with an air passage in the cylinder of piston 90. When the piston main body of piston 90 is pushed from the normal position where it is projected, the air inlet and outlet ports are switched to be closed, and the water inlet and outlet ports are switched to be open. A supply port and an exhaust port are respectively formed in the cylinder 92. When the piston main body of piston 92 is held at a normal position where it is projected, the supply port is kept disconnected from the exhaust port. When the piston main body of piston 92 is pushed from the normal position where it is projected, the supply port is switched to communicate with the exhaust port.

Figure 17:
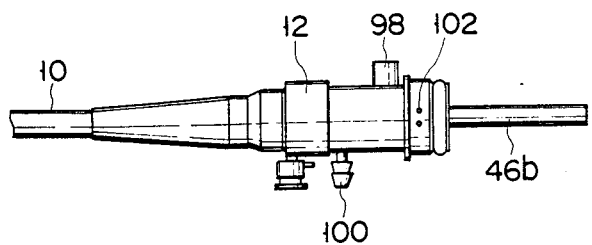
FIG. 17 is a side view of an endoscope connector according to the first embodiment.

As shown in FIG. 17, water-supply plug 100, suction plug 102, and electrical contact 104 are respectively disposed on the outer surface of connector 12. A connecting end portion of portion 46b of bundle 46 and air-supply pipe 106 are respectively provided on the distal end face of connector 12. When connector 12 is connected to the light source unit, the connecting end portion of portion 46b is connected to a light supply portion, and pipe 106 is connected to an air-supply mechanism in the light source unit. Plug 100 is connected to the water inlet port of piston 90 through a water-supply path formed in cord 10, and pipe 106 is connected to the air inlet port of piston 90 through an air-supply path in cord 10. In addition, plug 102 is connected to the exhaust port of piston 92 through a suction path in cord 10.

Piston 90 is selectively switched to a normal position where air supplied from an air supply source in the light source unit to portion 4 through connector 12 and cord 10 is exhausted outward through the air exhaust hole, to an exhaust position where air supplied from the air supply source in the light source unit to portion 4 through connector 12 and the air-supply path in cord 10 is supplied to pipe 48 in portion 6, and to a water-supply position where piston 90 is pushed while the air exhaust hole of piston 90 is kept closed by a finger and the like of a user, the air-supply path in cord 10 is closed, air supplied from the air supply source in the light source unit is supplied into a water-supply tank connected to plug 100 of connector 12 to pressurize an interior of the water-supply tank, and water supplied from the water-supply tank is supplied to pipe 48 in portion 6 through cord 10 and the water-supply path in portion 4. In addition, a suction path can be opened/closed by piston 92.

Portion 8 includes water-supply switching cock 108, suction switching cock 110, and lure-lock plug 112. A cock main body and a pivoting member pivotally incorporated in the cock main body are provided to each of cocks 108 and 110. In addition, first, second, and third coupling end portions are formed to the cock main body of cock 108, and fourth, fifth, and sixth coupling end portions are formed in the cock main body of cock 110. The first coupling end portion of cock 108 is coupled to the water outlet port of piston 90, and the third coupling end portion is coupled to pipe 82. The fourth coupling end portion of cock 110 is coupled to channel 44, and the sixth coupling end portion is coupled to pipe 84. A first coupling hole for coupling the first coupling end portion with the second coupling end portion, and a second coupling hole for coupling the first coupling end portion with the third coupling end portion while the pivoting member is kept pivoted through a predetermined angle from an optical system washing position where the first coupling end portion is coupled to the second coupling end portion through the first coupling hole, are formed in the pivoting member of cock 108. Upon a pivoting operation of the pivoting member, a switching operation can be selectively performed from the optical system washing position to a balloon water-supply position where the first coupling end portion is coupled to the third coupling end portion through the second coupling hole. In addition, the second coupling end portion of cock 108 is coupled to the air outlet port of piston 90. Furthermore, a third coupling hole for coupling the fourth coupling end portion with the fifth coupling end portion, and a fourth coupling end hole for coupling the fourth coupling end portion with the sixth coupling end portion while the pivoting member is kept pivoted through a predetermined angle from an endoscope suction position where the fourth coupling end portion is coupled to the fifth coupling end portion through the third coupling hole, are formed in the pivoting member of cock 110. Therefore, upon a pivoting operation of the pivoting member, a switching operation can be performed from the endoscope suction position to balloon suction position where the fourth coupling end portion is coupled to the sixth coupling end portion through the third coupling hole.

Figure 18:
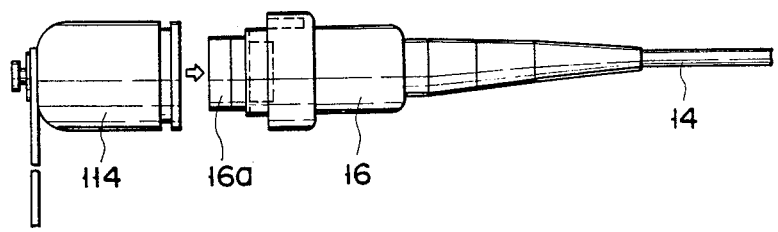
FIG. 18 is a side view of an electrical connector according to the first embodiment.
Figure 19:
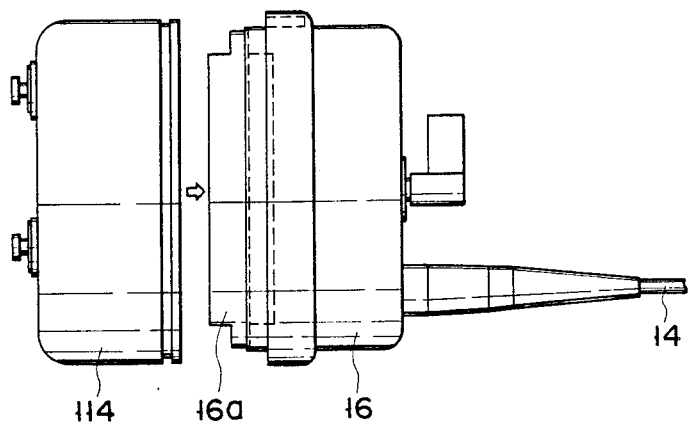
FIG. 19 is a plan view of the electrical connector shown in FIG. 18.

As shown in FIGS. 18 and 19, waterproof cap 114 is detachably incorporated in connector 16 coupled to connector 12 through cord 14 so as to seal contact portion 16a of connector 16 in a water-tight state. In addition, a matching coil is incorporated in connector 16 so as to establish electrical matching between vibrator 26 and the ultrasonic observing unit. By changes in conditions such as frequency of vibrator 26 and a length from portion 22 to connector 16 of endoscope 2, which vary depending on the types of endoscope 2, the electrical matching between each type of endoscope 2 and the ultrasonic observing unit is adjusted beforehand by the matching coil in connector 16. Furthermore, a probe detecting means for representing characteristic items according to types of probe (endoscope 2), i.e., a difference between an insertion probe and a contact probe, a frequency of vibrator 26 incorporated in portion 22, a difference between electronic sector and electronic linear vibrators, and a difference between directions of slices in the electronic sector type (a difference between ultrasonic vibrator 26a for a longitudinal slice shown in FIG. 20 and ultrasonic vibrator 26b for a cross-sectional slice shown in FIG. 21), is incorporated in connector 16. The probe detecting means is constituted by a detecting section for detecting changes in an electrical resistance and an ON/OFF state of a contact pin, an electrical circuit including a memory section (ROM), and the like.

Figure 9:
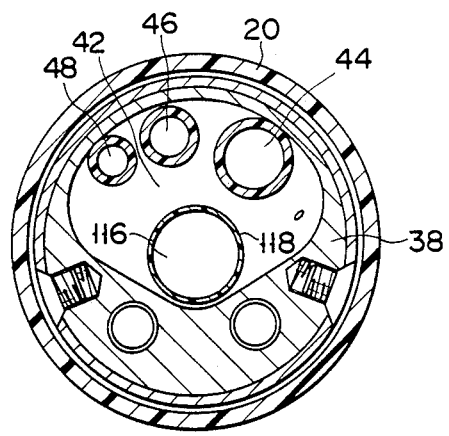
FIG. 9 is a cross-sectional view of the hard distal end portion of the endoscope taken along the line IX—IX in FIG. 3.
Figure 10:
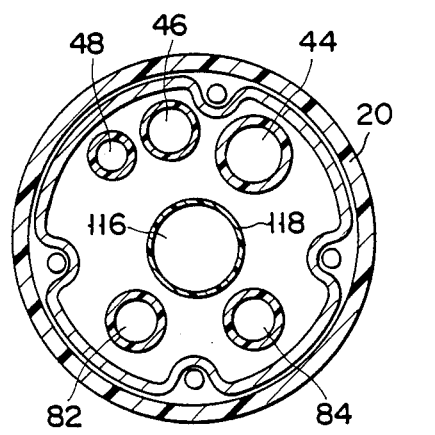
FIG. 10 is a cross-sectional view of the hard distal end portion of the endoscope taken along the line X—X in FIG. 3.
Figure 11:
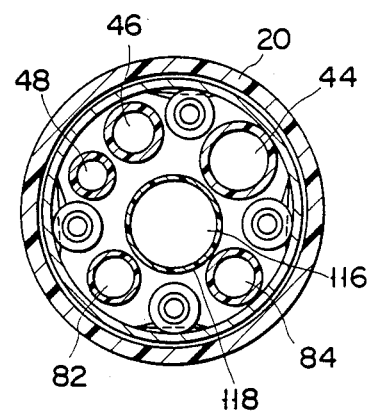
FIG. 11 is a cross-sectional view of the hard distal end portion of the endoscope taken along the line XI—XI in FIG. 3.

As shown in FIGS. 9 to 11, bundle 116 of an electrical cable (Al shield wire) of vibrator 26 is coated with protective tube 118 such as a silicone tube.

When endoscope 2 is used, portion 6 is inserted in a body cavity, portion 22 is guided to an objective portion, the pivoting member of cock 108 of portion 8 is pivoted to the balloon water-injection position, the pivoting member of cock 110 thereof is pivoted to the balloon suction position, the piston main body of piston 90 is pushed while the air exhaust hole of piston 90 of portion 4 is kept closed by a finger and the like of the user, and the piston main body of piston 92 is pushed to the suction position, thereby injecting water in balloon 74. Thereafter, the ultrasonic wave is scanned by vibrator 26 while water is kept filled in balloon 74 to obtain a tomographic image of, e.g., a body cavity wall.

In the endoscope having the above arrangement, portion 60 to be fitted on the distal end portion outer surface of holder 38 for holding vibrator 26 and hole 62 are respectively formed in holder 40 for holding system 30, and screw 64 is threadably engaged with hole 56a of member 56 of holder 38 while portion 60 of holder 40 is kept fitted on the distal end portion outer surface of holder 38. Therefore, by untightening screw 64, holder 40 can be detached from holder 38. For this reason, by using endoscope 2, when bundle 46 of system 30 is damaged, holder 38 for holding vibrator 26 can be separated from holder 40 for holding system 30. As a result, only damaged bundle 46 of system 30 can be replaced, so that expensive vibrator 26 which normally operates need not be replaced together with the damaged bundle of optical fibers unlike in a conventional endoscope and can be used again, thereby reducing repairing cost.

In addition, hole 42 having a relatively wide opening area is formed in holder 38 so as to extend from the front end face to the rear end face thereof, and channel 44, bundle 46 such as the light guide and the image guide of system 30, pipe 48, and the like are provided in hole 42. For this reason, during an attaching/detaching operation of holder 40, attaching/detaching operations of channel 44, bundle 46 such as the light guide and the image guide of system 30, pipe 48, and the like can be easily performed.

Furthermore, plate 52 is disposed between vibrator 26 held by portion 50 of holder 38 and hole 42. For this reason, an opening area of hole 42 can be enlarged. In addition, hole 42 can be easily formed in holder 38.

Figure 20:
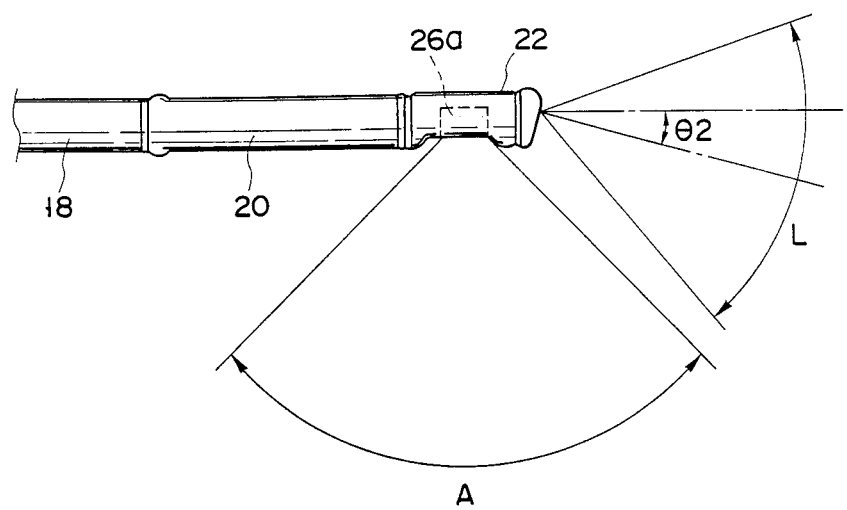
FIG. 20 is a side view showing a diagnostic range obtained when an electronic sector type ultrasonic vibrator for a longitudinal slice is used as the ultrasonic vibrator according to the first embodiment.
Figure 21:
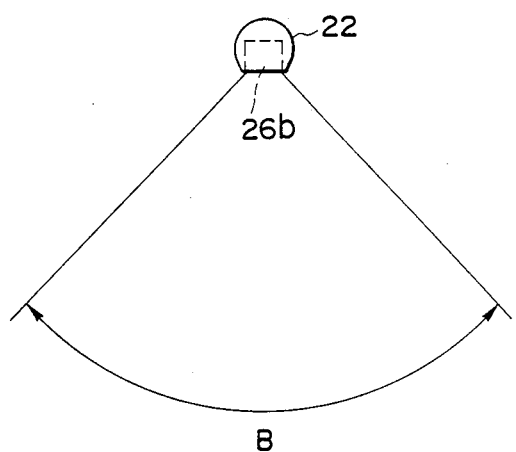
FIG. 21 is a front view showing a diagnostic range obtained when an electronic sector type ultrasonic vibrator for a cross-sectional slice is used as the ultrasonic vibrator according to the first embodiment.

Moreover, since recess 34 is formed on the side surface of body 24 and surface 26a of vibrator 26 is formed on the inner bottom portion of recess 34 and exposed outwardly, an outer diameter of body 24 can be reduced. In addition, inclined portions 36a and 36b are formed at the front and rear side surfaces of recess 34 of body 24 such that a front-to-rear interval therebetween is gradually increased outwardly from the inner bottom portion. Therefore, when electronic sector type ultrasonic vibrator 26a for a longitudinal slice is incorporated in body 24, its diagnostic range represented by symbol A in FIG. 20 is not narrowed by both the side surfaces of recess 34 of body 24. Note that a diagnostic range obtained when electronic sector type ultrasonic vibrator 26a for a cross-sectional slice is incorporated in body 24 is represented by symbol B in FIG. 21.

The distal end face of body 24 is formed inclined at proper angle θ2 with respect to a direction orthogonal to an axial direction, and a light beam guided through portion 46b of bundle 46 is radiated from the distal end surface of portion 46b so as to be inclined at proper angle θ2 toward the mounting surface side of vibrator 26 with respect to a direction orthogonal to an axial direction of body 24. FIG. 20 shows radiation range L of portion 46b. Even when vibrator 26 is incorporated in a substantially central portion of body 24 and portion 46b of bundle 46 is mounted separate from a central portion of body 24, a visual field of portion 46a is not partially darkened, but uniform brightness of portion 46a can be obtained throughout the visual field.

Since ring-like portion 46b is disposed on the outer surface of portion 46a of bundle 46 forming system 30, the entire endoscope can be made smaller than an endoscope in which portions 46a and 46b in bundle 46 are made by different bundles of optical fibers.

In addition, since an adhesive having a good thermal conductivity such as "an epoxy adhesive mixed with a powder of SiC (silicon carbide)" is coated on the bonding surface between vibrator 26 and portion 50 of holder 38, heat from vibrator 26 can be easily dissipated toward portion 50, thereby preventing overheating of vibrator 26.

Furthermore, concave groove 76 provided along the circumferential direction is formed between the mounting portion of vibrator 26 at the outer surface of holder 38 and groove 72b, and the balloon water-injection hole and the balloon suction hole are coupled to groove 76. Therefore, when air in balloon 74 is sucked, balloon 74 is sucked inside the balloon suction hole, so that the balloon suction hole does not clog.

Moreover, switch 94 for remote-controlling an instrument such as a camera, and switch 96 for freezing an image of a monitor television set and the like of the ultrasonic observing unit are provided near pistons 90 and 92 of portion 4, respectively. Therefore, the user of endoscope 2 can easily operate the instrument such as a camera during the operation of endoscope 2, and image freezing on the monitor television set and the like of the ultrasonic observing unit can be easily performed.

In addition, the matching coil for establishing electrical matching between vibrator 26 and the ultrasonic observing unit is incorporated in connector 16. For this reason, by changes in conditions such as frequency of vibrator 26 different in accordance with types of endoscope 2 and a length from portion 22 of endoscope 2 to connector 16, the electrical matching between each type of endoscope 2 and the ultrasonic observing unit can be adjusted by the matching coil in connector 16. Therefore, a switching operation for establishing electrical matching in accordance with types of endoscope 2 need not be performed by the ultrasonic observing unit. Furthermore, since the probe detecting means for representing characteristic items corresponding to types of probe is incorporated in connector 16, a type of endoscope 2 or the characteristic items corresponding to types thereof can be displayed on a screen of the monitor television set and the like of the ultrasonic observing unit and switching of electrical matching can be automatically performed while connector 16 of endoscope 2 is kept connected to the ultrasonic observing unit.

Figure 23:
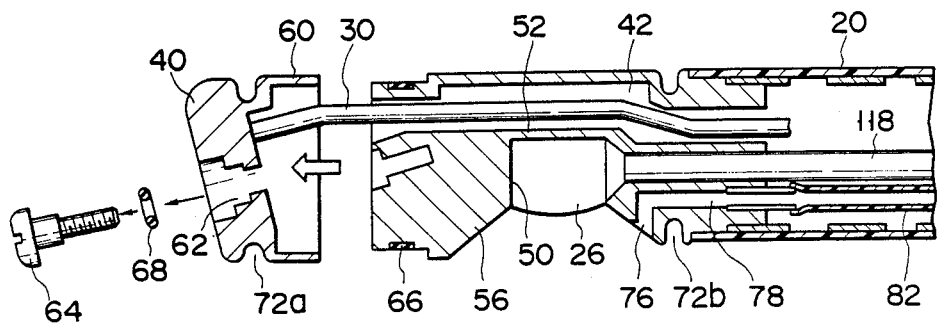

The present invention is not limited to the above embodiment. For example, as a first modification of the first embodiment shown in FIGS. 22 and 23, plate 52 disposed between vibrator 26 held by portion 50 and hole 42, member 56 embedded in the notch portion formed in holder 38 at the front side portion of portion 50, and holder 38 may be integrally formed.

Figure 24:
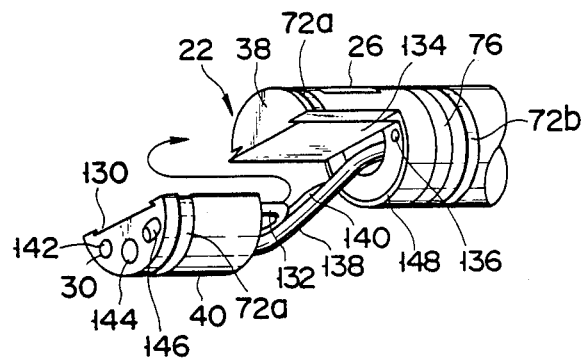
FIG. 24 is a perspective view of a second modification of the hard distal end portion.

FIG. 24 shows a second modification. In the second modification, first holder 38 for holding array type ultrasonic vibrator 26 is formed in a semicircular portion of substantially pillar-like hard distal end portion 22, second holder 40 for holding forward-view (direct-view or oblique-view) type observing optical system 30 is formed in the other semicircular portion, groove 130 and engaging pawl 132 are provided to holder 40, engaging projection 134 and engaging hole 136 for engaging with groove 130 and pawl 132 are respectively provided to holder 38, and holder 38 and holder 40 for holding system 30 are detachably coupled together. Light guide 138 and image guide 140 in system 30 are formed by different bundles of optical fibers, respectively. Illumination lens 142 disposed to oppose the distal end face of guide 138, objective lens 144 disposed to oppose the distal end face of guide 140, and air-supply/water-supply nozzle 146 are respectively disposed on the distal end face of holder 40. In addition, sealing member 148 is mounted on a bonding portion of holder 38 with respect to holder 40, thereby maintaining air-tight and water-tight sealing between holders 38 and 40.

Figure 25:
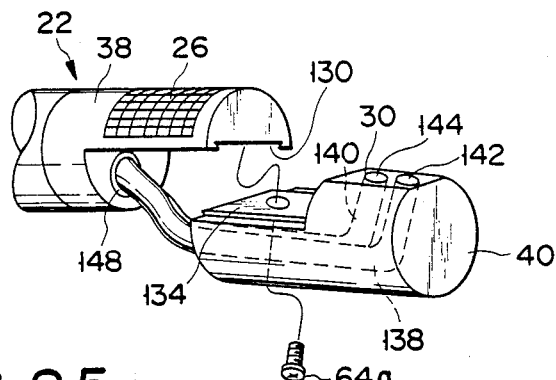
FIG. 25 is a perspective view of a third embodiment of the hard distal end portion.

FIG. 25 shows a third modification. In the third modification, lens 142 disposed to oppose the distal end face of of guide 138 in system 30, and lens 144 disposed to oppose the distal end face of guide 140 are disposed on the outer surface of holder 40 in the second modification, thereby forming side-view type observation optical system 30. In addition, groove 130 is formed in holder 38, projection 134 for engaging with groove 130 is formed in holder 40, and holder 40 is fixed to holder 38 by screw 64a while projection 38 of holder 40 is kept engaged with groove 130 of holder 38.

Therefore, the same effect as that of the first embodiment can be obtained by the above first, second, and third modifications.

Figure 26:
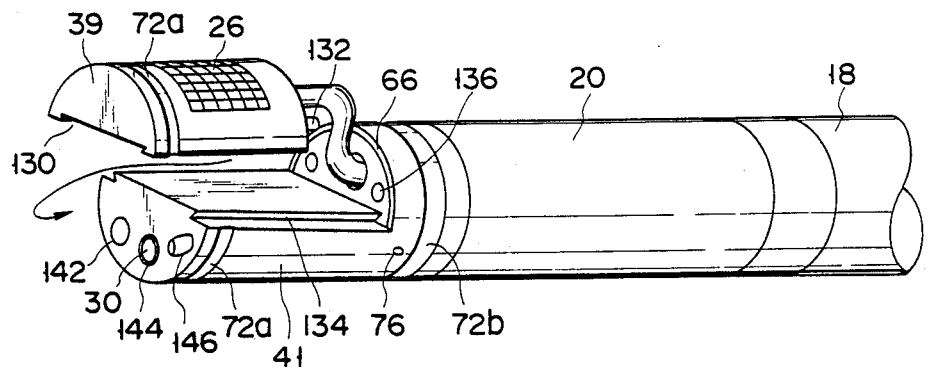
FIG. 26 is a perspective view of a fourth modification of the hard distal end portion.

FIG. 26 shows a fourth modification. In the fourth embodiment, first holder 39 having substantially the same arrangement as that of holder 38 in the second modification shown in FIG. 24 and second holder 41 having substantially the same arrangement as that of holder 40 in the second modification are respectively provided. Vibrator 26 is incorporated in holder 39, and forward-view (direct-view or oblique-view) type observation optical system 30 is incorporated in holder 41.

Figure 27:
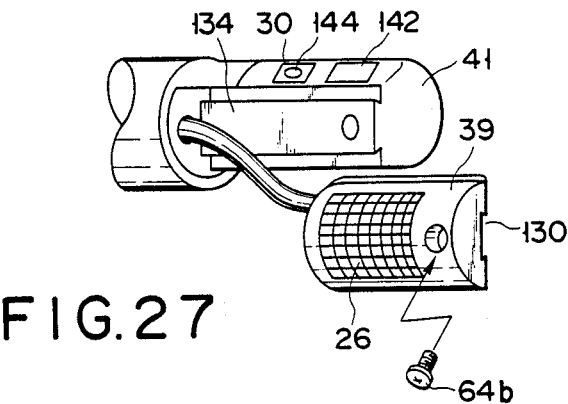
FIG. 27 is a perspective view of a fifth modification of the hard distal end portion.

FIG. 27 shows a fifth modification. In the fifth modification, side-view type observation optical system 30 is incorporated in holder 41 in the fourth embodiment, and holder 39 is fixed to holder 41 by screw 64b while projection 134 of holder 41 is kept engaged with groove 130 of holder 39.

Figure 28:
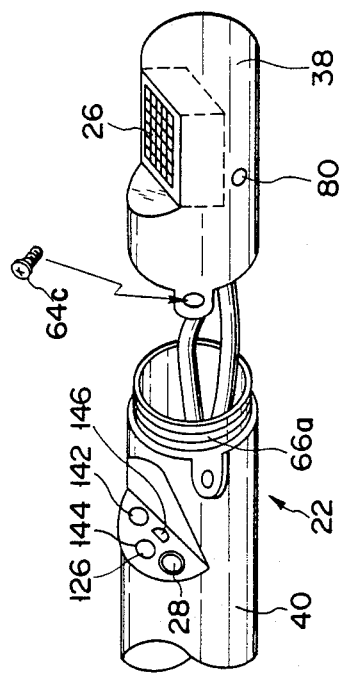
FIG. 28 is a perspective view of a sixth modification of the hard distal end portion.

FIG. 28 shows a sixth modification. In the sixth modification, first holder 38 for holding vibrator 26 is formed at the distal end portion of hard distal end portion 22, and second holder 40 for holding forward oblique-view type observation optical system 30 is formed behind holder 38. First and second holders 38, 40 are secured to each other with screws 64c. Seal 66a provides a water tight connection therebetween.

Therefore, the same effect as that of the first embodiment can be obtained by the above fourth, fifth, and sixth modifications. In addition, different types of vibrators 26 can be selectively incorporated in single endoscope 2. For example, electronic sector type vibrator 26 may be replaced with electronic linear type vibrator 26 and vice versa, or a plurality of electronic sector type vibrators 26 having different directions of slices (a longitudinal slice or a cross-sectional slice) may be replaced with each other, thereby changing directions of slices.

Figure 30:
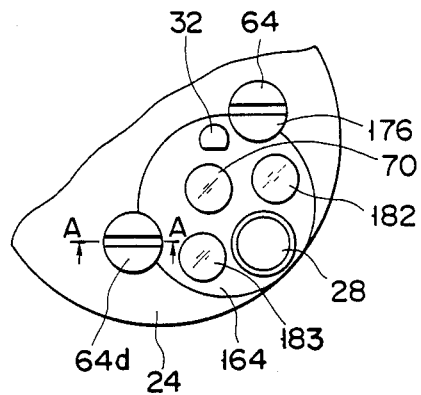
FIG. 30 is a front view showing a distal end face of an observation optical system of the distal end portion according to the second embodiment.
Figure 31:
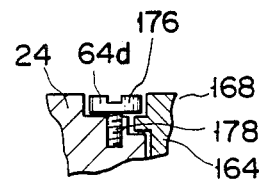
FIG. 31 is a partial sectional view of a locking member taken along the line A—A in FIG. 30.

The second embodiment of the present invention will now be described with reference to FIGS. 29 to 31.

Figure 29:
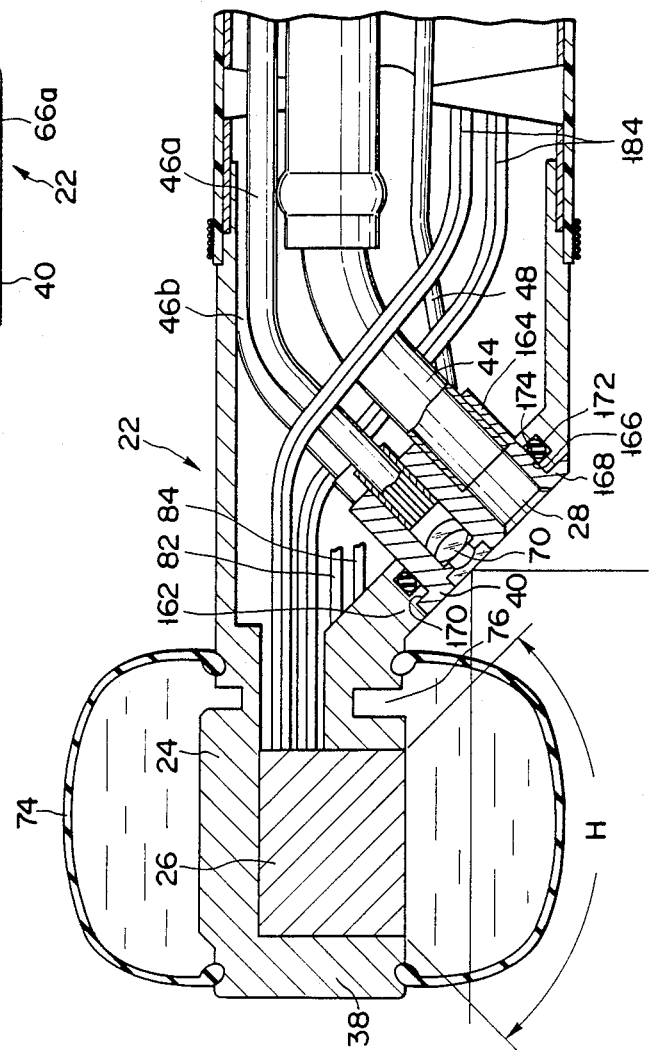
FIG. 29 is a longitudinal sectional view showing a hard distal end portion of an ultrasonic endoscope according to a second embodiment of the present invention.

FIG. 29 shows distal end constituting portion 22 of an insertion portion of an ultrasonic endoscope. Electronic sector scanning type ultrasonic vibrator 26 is embedded in the distal end and faces hard main body 24 of portion 22. Balloon 74 is air-tightly mounted on the distal end portion of body 24 having vibrator 26 and surrounds it. Groove-like port portion 76 is formed in balloon 74, and water-supply tube 82 and suction tube 84 are connected to portion 76. Water is supplied to balloon 74 from tubes 82 and 84 through portion 76 to expand balloon 74. Water in balloon 74 is sucked from tube 84 through portion 76 to contract balloon 74. Tubes 82 and 84 extend toward a manipulating portion through an insertion portion.

Inclined portion 162 is formed in a position nearer the manipulating portion from an installation position of vibrator 26 and is inclined toward ultrasonic scanning range H of vibrator 26. An outer wall surface of portion 162 is inclined at 45° with respect to a longitudinal axis of the insertion portion. Opening portion 166 is formed in a wall of portion 162 to detachably incorporate optical system holder 164. Collar 168 is formed at an outer periphery edge of holder 164 and is fitted in large-diameter portion 170 formed at an outer edge of portion 166, so that holder 164 is fitted tightly in portion 166. An outer surface of holder 164 constitutes a part of the outer wall surface of portion 162. O-ring 174 as a sealing member fitted in groove 172 formed in an inner surface portion of portion 166 seals air-tightly and water-tightly between holder 164 and portion 166. Collar 168 of holder 164 is tightened and fixed to the wall of portion 162 by locking members 64d each consisting of machine screw 178 with large head 176. That is, members 64 are provided at two positions, a left side and an upper portion, as shown in FIG. 30. As shown in FIG. 31, each member 64 is screwed in body 24 of portion 22, and each head 176 urges collar 168 of holder 164, thereby fixing holder 164.

Holder 164 includes lens 70, illumination lenses 182 and 183, forceps port 28, and nozzle 32 opposing the outer surface of lens 70. In addition, image guide optical fiber bundle 46a optically connected to lens 70, and two light guide optical fiber bundle 46b respectively optically connected to lenses 182 and 183 are mounted and fixed to holder 164. Connecting pipe 44 communicating with port 28 is mounted on holder 164, and tube 48 communicating with nozzle 32 is connected to holder 164. That is, bundles 46a and 46b, pipe 44, and tubes 48 and 45 are mounted on holder 164, and hence can be detached together when holder 164 is removed. Each of these elements extends to the manipulating portion through the insertion portion of the endoscope. Bundle 46a is coupled to an eyepiece of the manipulating portion. Bundles 46b reach a connector portion through the manipulating portion and a universal cord. This is the same with tube 48 communicating with nozzle 32. Tube 45 is connected to the forceps port of the manipulating portion.

On the other hand, electrical cable 184 extended from vibrator 26 similarly extends to the manipulating portion through the insertion portion of the endoscope and is connected to the connector portion through the manipulating portion and the universal cord.

Therefore, when either or both of bundles 46a and 46b in the endoscope are damaged, member 180 is detached, and holder 164 is detached from portion 166 and pulled outside from body 24 of portion 22. As a result, bundles 46a and 46b and the like can be integrally pulled out, thereby replacing the damaged components with new ones. Components to be replaced are not limited to bundles 46a and 46b.

Figure 32:
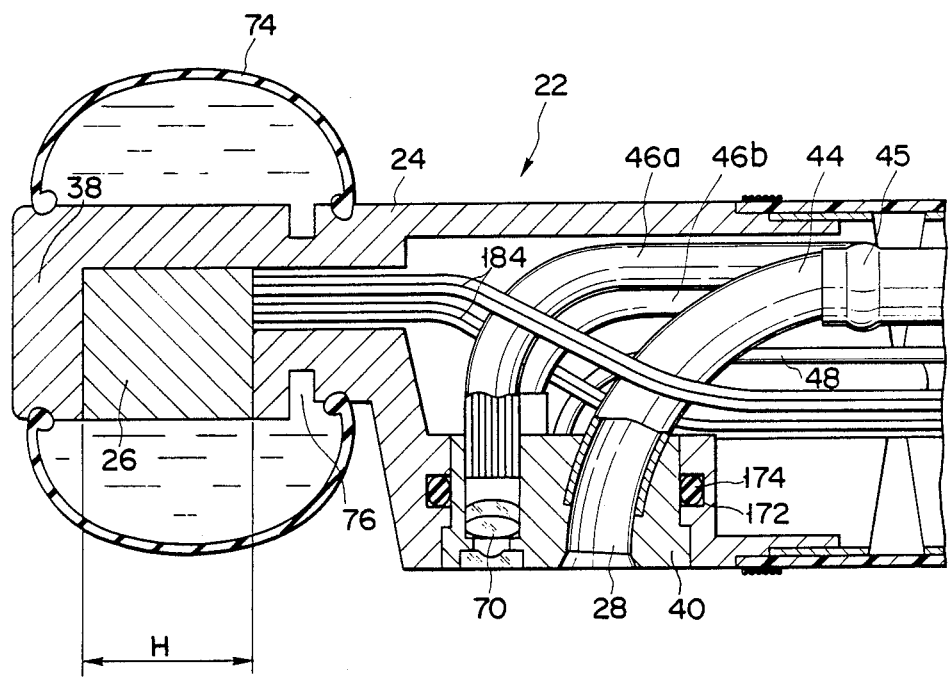
FIG. 32 is a longitudinal sectional view showing a modification of the hard distal end portion of the ultrasonic endoscope according to the second embodiment of the present invention.
Figure 33:
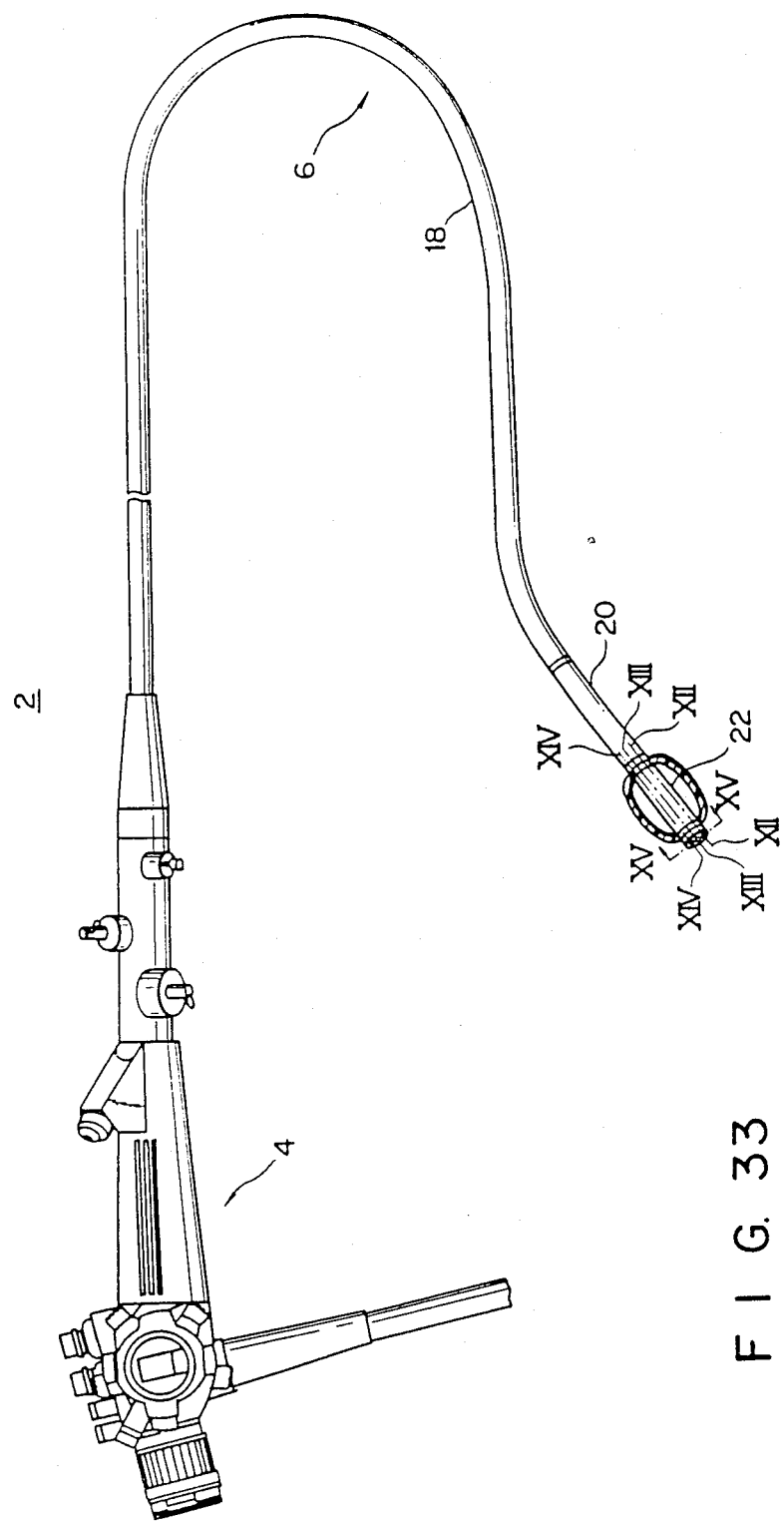
FIG. 33 is a perspective view of the overall outer appearance of an ultrasonic endoscope according to the present invention.

FIG. 32 shows a modification of the second embodiment. This modification uses an electronic linear scanning type ultrasonic vibrator and has a side-view optical observation direction. Other arrangements are the same as those of the above embodiment.

Note that the present invention is not limited to the above embodiments and the modifications. For example, the present invention includes an endoscope having an ultrasonic vibrator scanning direction toward the distal end, an endoscope without a groove in which a balloon is incorporated, and the like. In addition, scanning system is not limited to an electronic one but may be a mechanical one, i.e., may be variously modified and carried out without departing from the spirit and scope of the present invention.

What is claimed is:

1. An ultrasonic endoscope including an insertion portion having a hard distal end portion and a soft portion, and a manipulating portion connected to said insertion portion, said endoscope comprising:
    a first holding member provided at said hard distal end portion and connected to said soft portion, said first holding member having a holding section for fixation of an ultrasonic vibrator, and a through-hole communicating with the inside space of said soft portion;
    an ultrasonic vibrator attached to said holding member;
    an electric cable connected to said ultrasonic vibrator, said electric cable extending through said through-hole and the inside space of said soft portion;
    a second holding member provided at said hard distal end portion and being removably attached to said first holding member;
    an observation optical system having image transmission means and illumination means, and having an end portion fixed on said second holding member, said observation optical system extending through the inside space of said first holding member and the inside space of said soft portion, and said observation optical system being removable from the ultrasonic endoscope along with said second holding member; and
    fixing means for removably attaching said second holding member to said first holding member.

2. An endoscope according to claim 1, wherein said fixing means comprises a screw member.

3. An endoscope according to claim 2, further comprising a sealing member, disposed between said first and second holding members, for maintaining air-tight and water-tight sealing therebetween.

4. An endoscope according to claim 3, wherein said second holding member for holding said observation optical system is disposed at the distal end of said first holding member for holding said ultrasonic vibrator, and said observation optical system is guided to said manipulating portion through a space inside said first holding member.

5. The ultrasonic endoscope according to claim 4, wherein the inside space of the first holding member, into which said observation optical system is inserted, is formed behind a rear surface of the ultrasonic vibrator.

6. An endoscope according to claim 3, wherein said first and second holding members have respective facing surfaces separated from each other with respect to a plane parallel to a central axis of said insertion portion.

7. An apparatus according to claim 1, wherein said first holding member has an opening portion behind a position where said ultrasonic vibrator is mounted, and said fixing means includes means for detachably fitting said second holding member in said opening portion.

8. An endoscope according to claim 7, further comprising a sealing member, disposed between said first and second members, for maintaining air-tight and water-tight sealing therebetween.

9. The ultrasonic endoscope according to claim 1, further comprising an air-supply/water-supply/suction channel tube having one end portion fixed on said second holding member.

10. The ultrasonic endoscope according to claim 1, further comprising a balloon arranged so as to surround said ultrasonic vibrator.

* * * * *